United States Patent
Rickheim et al.

(10) Patent No.: US 11,382,663 B2
(45) Date of Patent: Jul. 12, 2022

(54) BIOSTIMULATOR RETRIEVAL SYSTEM HAVING CINCHER TUBE

(71) Applicant: Pacesetter, Inc., Sylmar, CA (US)

(72) Inventors: David Rickheim, Bloomington, MN (US); Daniel Coyle, St. Louis, MN (US); Adam Weber, Minnetonka, MN (US)

(73) Assignee: PACESETTER, INC., Sylmar, CA (US)

( * ) Notice: Subject to any disclaimer, the term of this patent is extended or adjusted under 35 U.S.C. 154(b) by 298 days.

(21) Appl. No.: 16/450,640

(22) Filed: Jun. 24, 2019

(65) Prior Publication Data
US 2020/0345396 A1 Nov. 5, 2020

Related U.S. Application Data

(60) Provisional application No. 62/843,130, filed on May 3, 2019.

(51) Int. Cl.
*A61B 17/50* (2006.01)
*A61N 1/375* (2006.01)
(Continued)

(52) U.S. Cl.
CPC .......... *A61B 17/50* (2013.01); *A61B 17/3468* (2013.01); *A61N 1/3756* (2013.01);
(Continued)

(58) Field of Classification Search
CPC ... A61B 17/221; A61B 17/50; A61B 17/3468; A61B 2017/00358; A61B 2017/003; A61B 2017/00367; A61N 1/05; A61N 1/37518
(Continued)

(56) References Cited

U.S. PATENT DOCUMENTS

| 5,098,440 A | 3/1992 | Hillstead |
| 5,897,537 A * | 4/1999 | Berg ............... F16L 9/147 604/525 |

(Continued)

FOREIGN PATENT DOCUMENTS

| DE | 8707515 U1 | 7/1987 |
| FR | 2694687 A1 | 2/1994 |

(Continued)

*Primary Examiner* — Kathleen S Holwerda
*Assistant Examiner* — Lauren Dubose
(74) *Attorney, Agent, or Firm* — Womble Bond Dickinson (US) LLP

(57) ABSTRACT

A retrieval system for a biostimulator, such as a leadless cardiac pacemaker, is described. The biostimulator retrieval system includes a docking cap rotatably coupled to an outer catheter by a bearing. A torque shaft extends through the outer catheter and attaches to the docking cap to transmit torque to the docking cap to cause rotation of the docking cap relative to the outer catheter. The rotating docking cap can transmit torque to an attachment feature of a biostimulator received within the docking cap. The attachment feature can be captured by a snare that extends through the torque shaft. A cincher tube extends through the torque shaft around the snare, and advances over the snare independently from the torque shaft that is attached to the docking cap, to cinch the snare onto the attachment feature. Other embodiments are also described and claimed.

19 Claims, 9 Drawing Sheets

(51) Int. Cl.
*A61B 17/34* (2006.01)
*A61B 17/00* (2006.01)

(52) U.S. Cl.
CPC .............. *A61B 2017/00358* (2013.01); *A61B 2017/00367* (2013.01)

(58) Field of Classification Search
USPC .................. 606/129, 113, 114, 127; 604/525
See application file for complete search history.

(56) References Cited

U.S. PATENT DOCUMENTS

| | | | |
|---|---|---|---|
| 6,626,915 | B2 | 9/2003 | Leveillee |
| 7,780,646 | B2 * | 8/2010 | Farnholtz .......... A61M 25/0147 |
| | | | 604/523 |
| 8,974,470 | B2 | 3/2015 | Lampropoulos et al. |
| 9,039,713 | B2 | 5/2015 | Segermark |
| 9,446,248 | B2 | 9/2016 | Sheldon et al. |
| 9,480,850 | B2 | 11/2016 | Schmidt et al. |
| 9,492,674 | B2 | 11/2016 | Schmidt et al. |
| 9,539,016 | B2 | 1/2017 | Lampropoulos et al. |
| 9,566,673 | B2 | 2/2017 | Pham et al. |
| 10,188,425 | B2 | 1/2019 | Khairkhahan et al. |
| 2005/0209609 | A1 | 9/2005 | Wallace |
| 2012/0165827 | A1 * | 6/2012 | Khairkhahan ..... A61B 17/3468 |
| | | | 606/129 |
| 2015/0335884 | A1 | 11/2015 | Khairkhahan et al. |
| 2016/0067446 | A1 | 3/2016 | Klenk et al. |
| 2016/0213919 | A1 * | 7/2016 | Suwito ................ A61N 1/37205 |
| 2017/0319847 | A1 * | 11/2017 | Ho ....................... A61N 1/3756 |
| 2018/0104451 | A1 | 4/2018 | Kerns et al. |
| 2018/0104452 | A1 | 4/2018 | Goodman et al. |
| 2018/0178007 | A1 | 6/2018 | Shuros et al. |
| 2018/0280058 | A1 | 10/2018 | Meade et al. |
| 2018/0303513 | A1 | 10/2018 | Kerns et al. |
| 2018/0318590 | A1 * | 11/2018 | Kabe .................... A61N 1/3756 |
| 2018/0318591 | A1 | 11/2018 | Kabe et al. |

FOREIGN PATENT DOCUMENTS

| | | |
|---|---|---|
| WO | 92/05828 A1 | 4/1992 |
| WO | 95/05129 A1 | 2/1995 |

* cited by examiner

BIOSTIMULATOR RETRIEVAL SYSTEM HAVING CINCHER TUBE

PRIORITY

This application claims the benefit of U.S. Provisional Application No. 62/843,130, filed May 3, 2019. The patent application identified above is incorporated here by reference in its entirety to provide continuity of disclosure.

BACKGROUND

Field

The present disclosure relates to biostimulators and related transport systems and methods. More specifically, the present disclosure relates to systems for retrieving leadless biostimulators.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. The generator usually connects to a proximal end of one or more implanted leads, the distal end of which contains one or more electrodes for positioning adjacent to the inside or outside wall of a cardiac chamber. Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle." Even without persistent manipulation, subcutaneous pulse generators can exhibit erosion, extrusion, infection, disconnection, insulation damage, or conductor breakage at the wire leads. Although sub-muscular or abdominal placement can address some concerns, such placement involves a more difficult surgical procedure for implantation and adjustment, which can prolong patient recovery.

Leadless cardiac pacemakers incorporate electronic circuitry at a pacing site and eliminate leads, and thus, avoid the above-mentioned shortcomings of conventional cardiac pacing systems. Leadless cardiac pacemakers can be anchored at the pacing site, e.g., within a patient tissue, by an anchor. During retrieval of a leadless cardiac pacemaker from the patient, a retrieval system can capture and apply torque to the leadless cardiac pacemaker to unscrew the anchor from the target tissue.

SUMMARY

Existing transport systems used for retrieval of leadless cardiac pacemakers may have a torque shaft that is used to both cinch a snare onto a biostimulator and to transmit torque to the biostimulator through a docking cap when the biostimulator is docked therein. To accomplish both functions, the torque shaft is typically not attached to the docking cap, but rather, slides longitudinally over the snare in a distal direction relative to the docking cap to cinch the snare. The torque shaft can have a key feature that engages a slot in the docking cap to transmit torque to the docking cap when the torque shaft is retracted in a proximal direction relative to the docking cap and rotated. The torque shaft can be a tubular cable formed from metallic strands to achieve the torsional stiffness that is required for torque transmission. Selection of the cable structure can, however, have consequences. For example, when the torque shaft is advanced to cinch the snare, the metallic strands can slide in contact with the snare, and the strands can abrade. Abrasion of the torque shaft may increase a risk of device failure.

A biostimulator retrieval system, such as a catheter-based system for retrieving a leadless cardiac pacemaker, is provided. The biostimulator retrieval system has a torque shaft that is attached to a docking cap, and a cincher tube that is independently and longitudinally movable relative to the torque shaft. In an embodiment, the biostimulator retrieval system includes an outer catheter having an inner lumen, and the docking cap is rotatably coupled to the outer catheter by a bearing. The docking cap has a docking cavity to receive an attachment feature of a leadless cardiac pacemaker. The torque shaft extends through the inner lumen, and attaches to the docking cap. For example, the torque shaft can be fixed to the docking cap. Accordingly, rotation of the torque shaft within the outer catheter can transmit torque to the docking cap. The torque shaft has a shaft lumen in communication with the docking cavity. A cincher tube extends through the shaft lumen. The cincher tube can be independent from and longitudinally movable relative to the torque shaft. In an embodiment, the cincher tube has a tube lumen, and a snare extends through the tube lumen. The snare includes one or more snare loops for use in capturing an attachment feature of the leadless cardiac pacemaker. More particularly, moving the snare relative to the cincher tube can actuate the snare loop to grip the leadless cardiac pacemaker. The cincher tube can separate the snare from the torque shaft, e.g., the cincher tube can have a tube wall that is in sliding contact with the snare and the torque shaft. Isolating the snare from the torque shaft by the cincher tube can ease actuation of the snare and reduce a likelihood that the snare will abrade the torque shaft during actuation and retrieval of the leadless cardiac pacemaker. For example, a structure and material of the cincher tube provides a balance between flexibility and pushability to allow the cincher tube to secure the snare loops around the biostimulator attachment feature while preventing metal-to-metal contact between the snare and the torque tube that can lead to abrasion.

In an embodiment, a method of retrieving a leadless cardiac pacemaker using a biostimulator retrieval system is provided. A snare loop of a snare is placed over an attachment feature of a leadless cardiac pacemaker. A cincher tube of the biostimulator retrieval system is advanced over the snare to cause the snare to grasp the attachment feature. The snare is separated from a torque shaft by the cincher tube, and thus, advancement of the cincher tube to grasp the attachment feature does not involve sliding contact between the snare and the torque shaft. Abrasion of the torque shaft is thereby prevented by the cincher tube, which is independent from and longitudinally movable relative to the torque shaft. The torque shaft can be attached to a docking cap. In an operation, the attachment feature is retracted into a docking cavity of the docking cap. Retraction of the attachment feature includes moving the cincher tube independently from and longitudinally relative to the torque shaft. When the attachment feature is in the docking cavity rotational torque is applied from the torque shaft to the attachment feature through the docking cap to unscrew the leadless cardiac pacemaker from tissue of a patient.

The above summary does not include an exhaustive list of all aspects of the present invention. It is contemplated that the invention includes all devices, systems, and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
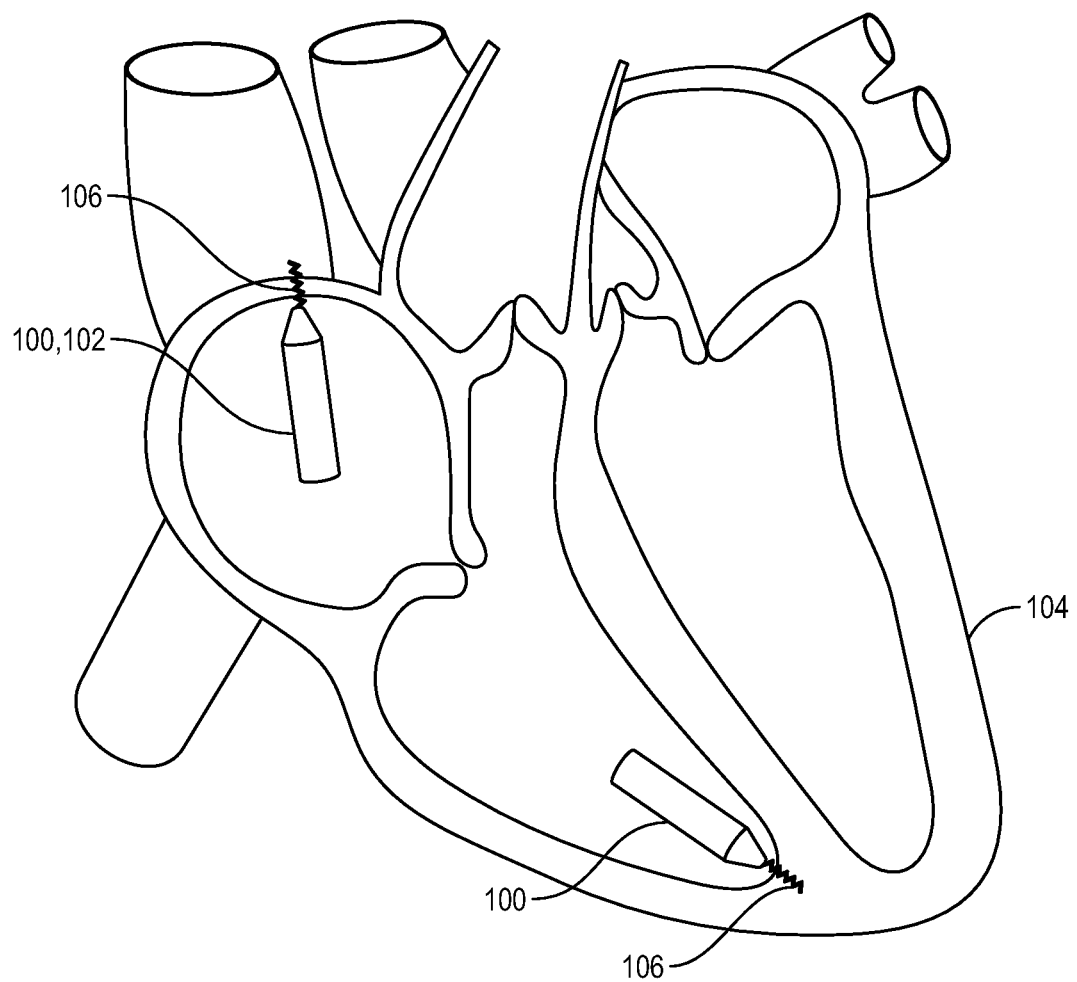
FIG. 1 is a diagrammatic medial-lateral cross section of a patient heart illustrating an example implantation of biostimulators in the patient heart, in accordance with an embodiment.

Embodiments describe a biostimulator retrieval system, e.g., a catheter-based system for retrieval of a biostimulator, having a torque shaft that is attached to a docking cap, and a cincher tube that is independently and longitudinally movable relative to the torque shaft. The biostimulator may be used to pace cardiac tissue, e.g., may be a leadless cardiac pacemaker, as described below. The biostimulator may, however, be used in other applications, such as deep brain stimulation, and thus, reference to the biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator retrieval system. Similarly, "proximal" may indicate a second direction opposite to the first direction. Such terms are provided to establish relative frames of reference, however, and are not intended to limit the use or orientation of a biostimulator retrieval system to a specific configuration described in the various embodiments below.

In an aspect, a biostimulator retrieval system is provided. The biostimulator retrieval system includes a docking cap to receive an attachment feature of a biostimulator, and the docking cap is rotatably coupled to an outer catheter. Rotation of the docking cap relative to the outer catheter is provided by a torque shaft that is attached directly to the docking cap. More particularly, the torque shaft can transmit torque directly to the docking cap through an attachment joint that fixes the torque shaft to the docking cap. The docking cap can therefore transmit the torque to the biostimulator when the attachment feature is docked within a docking cavity of the docking cap. Independently from the torque shaft, a cincher tube can move longitudinally through the torque shaft over a snare. The cincher tube can be axially stiff and flexible, and can have a solid inner surface that does not abrade when sliding over the snare. For example, the inner surface can be a solid polymeric surface, rather than a braided metallic strand surface. The cincher tube can separate or isolate the snare from the torque shaft, and can advance over the snare to cause the snare to grasp the attachment feature. The snare and the cincher tube can then be retracted to pull the attachment feature into the docking cap to allow the torque shaft to transmit the torque that unscrews the biostimulator from a target tissue site.

Referring to FIG. 1, a diagrammatic medial-lateral cross section of a patient heart illustrating an example implantation of biostimulators in the patient heart is shown in accordance with an embodiment. A cardiac pacing system includes one or more biostimulators 100. The biostimulators 100 can be implanted in the patient heart 104, and can be leadless, and thus may be leadless cardiac pacemakers 102. Each biostimulator 100 can be placed in a cardiac chamber, such as a right atrium and/or right ventricle of the patient heart 104, or attached to an inside or outside of the cardiac chamber. Attachment of the biostimulator 100 to the cardiac tissue can be accomplished via one or more fixation elements 106, such as helical anchors. In a particular embodiment, the leadless cardiac pacemaker 102 can use two or more electrodes located on or within a housing of the leadless cardiac pacemaker 102 for pacing the cardiac chamber upon receiving a triggering signal from internal circuitry and/or from at least one other device within the body.

Figures 2A, 2B:
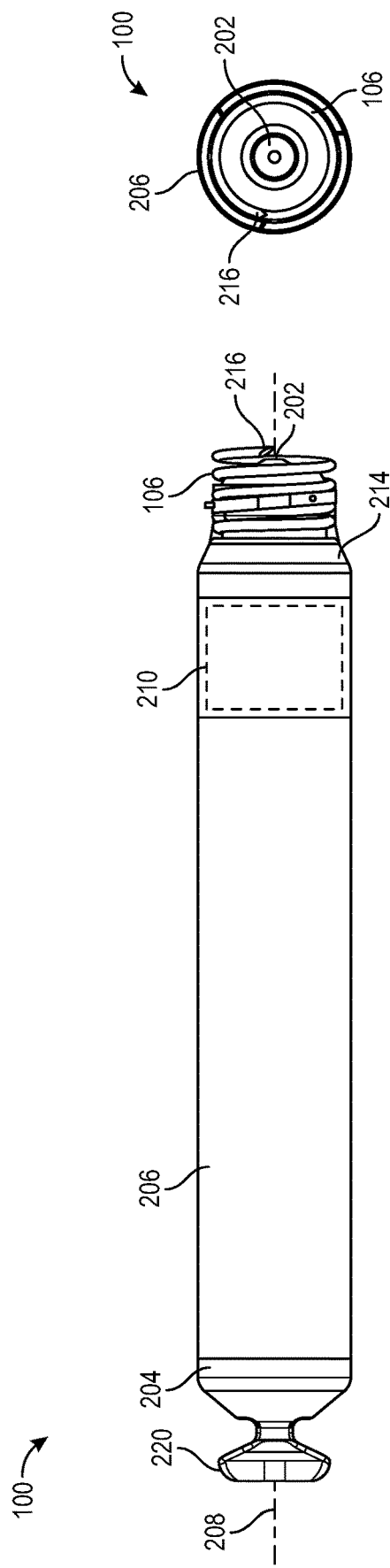
FIGS. 2A-2B are, respectively, side and end views of a biostimulator, in accordance with an embodiment.

Referring to FIG. 2A, a side view of a biostimulator is shown in accordance with an embodiment. The biostimulator 100 can be a leadless cardiac pacemaker 102 that can perform cardiac pacing and that has many of the advantages of conventional cardiac pacemakers while extending performance, functionality, and operating characteristics. The biostimulator 100 can have two or more electrodes, e.g., a distal electrode 202 and a proximal electrode 204, located within, on, or near a housing 206 of the biostimulator 100. In an embodiment, one or more of the fixation elements 106 forms a portion of the distal electrode 202. The electrodes can deliver pacing pulses to muscle of the cardiac chamber, and optionally, can sense electrical activity from the muscle. The electrodes may also communicate bidirectionally with at least one other device within or outside the body.

In an embodiment, the housing 206 has a longitudinal axis 208, and the distal electrode 202 can be a distal pacing electrode mounted on the housing 206 along the longitudinal axis 208. The housing 206 can contain a primary battery to provide power for pacing, sensing, and communication, which may include, for example bidirectional communication. The housing 206 can optionally contain an electronics compartment 210 to hold circuitry adapted for different functionality. For example, the electronics compartment 210 can contain circuits for sensing cardiac activity from the electrodes, circuits for receiving information from at least one other device via the electrodes, circuits for generating pacing pulses for delivery via the electrodes, or other circuitry. The electronics compartment 210 may contain circuits for transmitting information to at least one other device via the electrodes and can optionally contain circuits for monitoring device health. The circuit of the biostimulator 100 can control these operations in a predetermined manner. In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

Leadless pacemakers or other leadless biostimulators 100 can be fixed to an intracardial implant site by one or more actively engaging mechanisms or fixation mechanisms, such as a screw or helical member that screws into the myocardium. In an embodiment, the biostimulator 100 includes the fixation element 106 coupled to the housing 206. The fixation element 106 can be a helical element to screw into target tissue. More particularly, the fixation element 106 can extend helically from a flange 214 of the biostimulator 100, which is mounted on the housing 206, to a distal tip at a helix distal end 216.

Referring to FIG. 2B, an end view of a biostimulator is shown in accordance with an embodiment. The helix distal end 216 can be located distal to the distal electrode 202 (a centrally located electrode). Accordingly, when the biostimulator 100 contacts the target tissue, the distal tip can pierce the tissue and the housing 206 can be rotated to screw the outer fixation element 106 into the target tissue to pull the distal electrode 202 into contact with the tissue.

Leadless pacemakers or other leadless biostimulators 100 can be delivered to and retrieved from a patient using a biostimulator transport system. Referring again to FIG. 2A, the biostimulator 100 may include an attachment feature 220 to facilitate such delivery or retrieval. In general, the attachment feature 220 can include a fixed retrieval feature or "button" that is robust against the expected forces seen in vivo, that is fatigue resistant, and that provides control over the leadless pacemaker during delivery and retrieval. Each of these properties contributes to the overall effectiveness of the attachment feature 220, thereby reducing the likelihood of improper or incomplete implantation of the leadless pacemaker, breakage or damage to the leadless pacemaker, and, ultimately, potential damage to the patient's heart and associated tissue. The attachment feature 220 of the biostimulator 100 can be a fixed-post or a flexible docking button that protrudes from a proximal end of the biostimulator 100.

Figure 3:
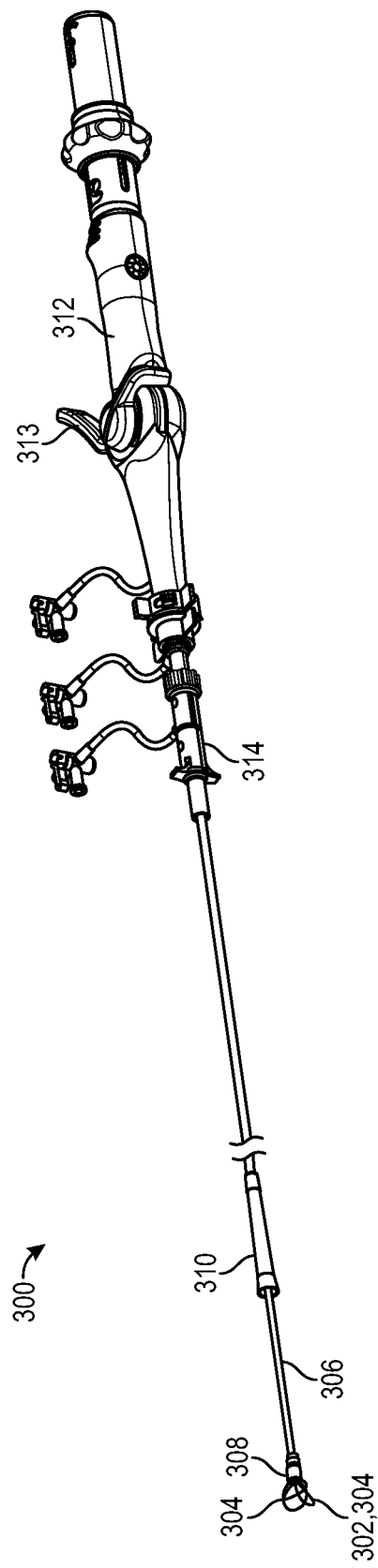
FIG. 3 is a perspective view of a biostimulator retrieval system, in accordance with an embodiment.

Referring to FIG. 3, a perspective view of a biostimulator retrieval system is shown in accordance with an embodiment. A biostimulator retrieval system 300 is a type of a biostimulator transport system used to retrieve the biostimulator 100 from the patient heart 104. The biostimulator retrieval system 300 can be advanced into the patient toward the biostimulator 100 that was previously delivered to a target tissue. More particularly, a snare 302 of the biostimulator retrieval system 300 can be advanced into a vicinity of the implanted biostimulator 100. The snare 302 can include one or more snare loops 304 that can be advanced distally outward from an outer catheter 306 to surround the attachment feature 220 of the biostimulator 100. When the snare 302 surrounds the attachment feature 220 of the pacemaker, a cincher tube, as described below, can be advanced distally along the snare 302 to close the snare 302, causing the snare 302 to grasp the attachment feature 220 of the biostimulator 100. Next, the snare 302 and cincher tube can be pulled proximally towards a docking cap 308 of the biostimulator retrieval system 300 to dock the attachment feature 220 within the docking cap 308. The attachment feature 220 can have a shape that engages a torque transmission feature of the docking cap 308. Accordingly, rotational torque can be applied to the attachment feature 220 by a torque shaft, as described below, via the docking cap 308 to unscrew the biostimulator 100 from the patient tissue. A protective sheath 310 can be advanced over the dislodged biostimulator 100, and the biostimulator 100 can then be removed from the patient.

The biostimulator retrieval system 300 can include a handle 312. The handle 312 can be connected to the outer catheter 306, the torque shaft, the cincher tube, and the snare 302, as described below. More particularly, the handle 312 can control relative movement between the retrieval system components. The outer catheter 306 extends distally from the handle 312. The outer catheter 306 can be a deflectable catheter, and an operator can use the handle 312 to steer the distal end in the patient, e.g., via a steering lever 313.

In an embodiment, the biostimulator retrieval system 300 includes the protective sheath 310 mounted on the outer catheter 306. The protective sheath 310 can be slidably disposed on the outer catheter 306 such that a distal portion of the protective sheath 310 can slide distally over the distal end of the outer catheter 306 and/or the biostimulator 100. Similarly, the biostimulator retrieval system 300 can include an introducer hub assembly 314 mounted on the protective sheath 310. The introducer hub assembly 314 can be slidably disposed on the protective sheath 310 such that a distal portion of the introducer hub assembly 314 can slide distally over the distal end of the outer catheter 306 and/or the distal portion of the protective sheath 310. More particularly, the introducer hub assembly 314 can be inserted into an access sheath to gain access to the patient vasculature, and after access is established, the distal portion of the protective sheath 310 and/or the distal end of the outer catheter 306 can be advanced through the access sheath into the patient.

Figure 4:
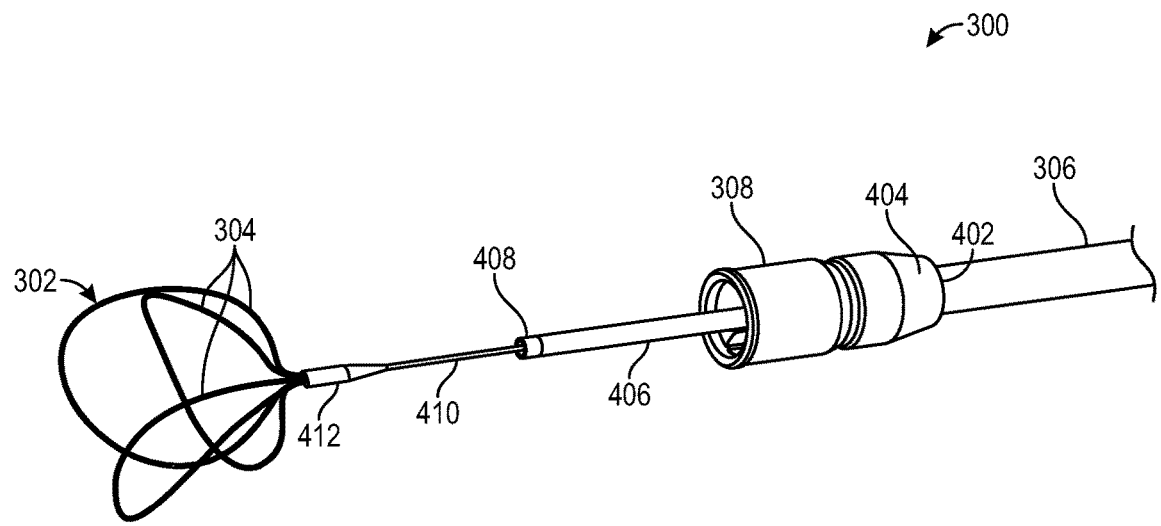
FIG. 4 is a perspective view of a distal portion of a biostimulator retrieval system, in accordance with an embodiment.

Referring to FIG. 4, a perspective view of a distal portion of a biostimulator retrieval system 300 is shown in accordance with an embodiment. The outer catheter 306 of the biostimulator retrieval system 300 can extend along a central axis to a distal catheter end 402. The outer catheter 306 can have a tubular elongated body extending from the handle 312 to the distal catheter end 402. A bearing housing 404 can be mounted on the distal catheter end 402. The bearing housing 404 can contain a bearing (FIG. 6) used to rotatably couple the docking cap 308 to the outer catheter 306. More particularly, the docking cap 308 can be axially constrained relative to the distal catheter end 402, however, the docking cap 308 can rotate about the central axis relative to the outer catheter 306.

In an embodiment, a cincher tube 406 extends through the outer catheter 306 to a distal cincher end 408. The cincher tube 406 can have a tubular elongated body extending along the central axis from the handle 312 to the distal cincher end 408. The structure of the cincher tube 406, as described further below, can balance pushability of the cincher tube 406 with profile and flexibility of the cincher tube 406. By doing so, the cincher tube 406 provides a robust tube to close the snare 302 around the attachment feature 220 during retrieval of the biostimulator 100.

The snare 302 can extend through the cincher tube 406 to the one or more snare loops 304. More particularly, the snare 302 can extend through a torque shaft within the outer catheter 306 and the docking cavity to the snare loop(s) 304. In an embodiment, the snare 302 includes a snare body 410. The snare body 410 can extend from the handle 312 to a snare joint 412. The snare body 410 can include a solid core shaft, a cable having wound or braided wires, or another elongated body. The snare joint 412 can be a bond, e.g., a weld or an adhesive joint, a coupling, or another connection that interconnects the snare body 410 to the one or more snare loops 304. For example, the snare joint 412 can include a tube that is crimped over an outer surface of the snare body 410 and the snare loop(s) 304 to join the structures.

The snare loop(s) 304 can include a tri-loop snare or a single-loop snare structure to grasp onto the attachment feature 220. More particularly, the snare loop(s) 304 of the snare 302 can be positioned around the attachment feature 220 to snare the biostimulator 100 with the biostimulator retrieval system 300 during the retrieval process. As shown in FIG. 4, a tri-loop snare structure expands broadly in an unconstrained configuration. For example, a working diameter of the unconstrained tri-loop structure on a transverse plane orthogonal to the central axis can be in a range of 17 to 23 mm, e.g., 20 mm. Thus, the tri-loop structure may be advantageous over the single-loop structure by increasing a likelihood that the snare 302 will hook onto the attachment feature 220 when the cincher tube 406 is advanced to collapse the snare loop(s) 304 and constrain the snare 302 against the attachment feature 220.

Figure 5:
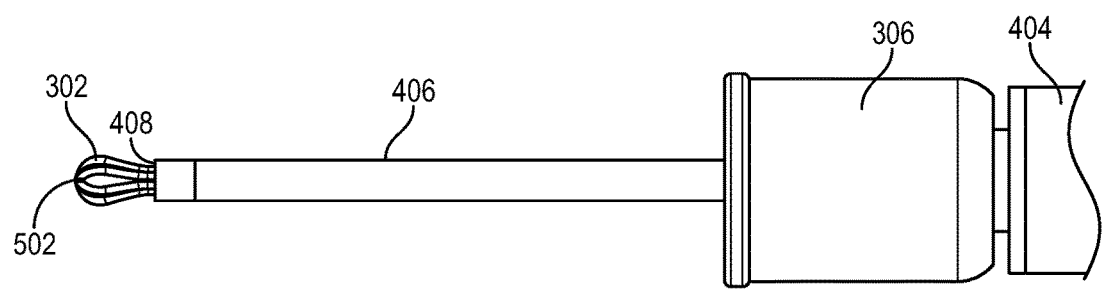
FIG. 5 is a side view of a distal portion of a biostimulator retrieval system, in accordance with an embodiment.

Referring to FIG. 5, a side view of a distal portion of a biostimulator retrieval system is shown in accordance with an embodiment. When the cincher tube 406 is advanced along the central axis relative to the docking cap 308, the distal cincher end 408 moves toward a distal snare end 502 of the snare 302. As the cincher tube 406 advances over the snare joint 412 and begins to ride over the snare loop(s) 304, the snare 302 begins to collapse. More particularly, a radial dimension of the snare 302 decreases as a longitudinal distance between the distal cincher end 408 and the distal snare end 502 decreases, until the snare 302 reaches the constrained configuration shown in FIG. 5. The distance between the distal cincher end 408 and the distal snare end 502 in the constrained configuration (when the cincher tube 406 is advanced fully in the distal direction) can be predetermined and controlled during manufacturing. For example, the cincher tube 406 and the snare 302 can be attached to the handle 312 at predetermined locations that ensure that, given each members respective length, full actuation of the cincher tube 406 in a distal direction by the handle 312 will result in the predetermined distance between the distal cincher end 408 and the distal snare end 502 at capture. The predetermined distance can be in a range of 0 to 4 mm. A protrusion length (distance between distal cincher end 408 and distal snare end 502) in the constrained configuration in a range of 1 to 3 mm, e.g., 2 mm, has been shown to reduce a likelihood that the attachment feature 220 will slip from the snare loop(s) 304 during retrieval while also reducing a likelihood that the cincher tube 406 will be compressed beyond its allowable maximum compression strength when pressing forward against the collapsed snare loop(s) 304.

A distance between the distal cincher end 408 and a distal end of the docking cap 308 in the constrained configuration can also be predetermined and controlled during manufacturing. For example, the cincher tube 406 and the outer catheter 306 can be attached to the handle 312 at predetermined locations that ensure that, given each members respective length, full actuation of the cincher tube 406 in the distal direction by the handle 312 will result in the predetermined distance between the distal cincher end 408 and the distal snare end 502 at capture. The predetermined distance can be in a range of 17 to 23 mm, e.g., 20 mm. That distance range has been shown to balance the ability of the docking cap 308 to dock to the attachment feature 220 with an appropriate amount of force to allow for torque transfer, with the ability to apply appropriate compressive forces on the catheter shafts during retrieval.

Figure 6:
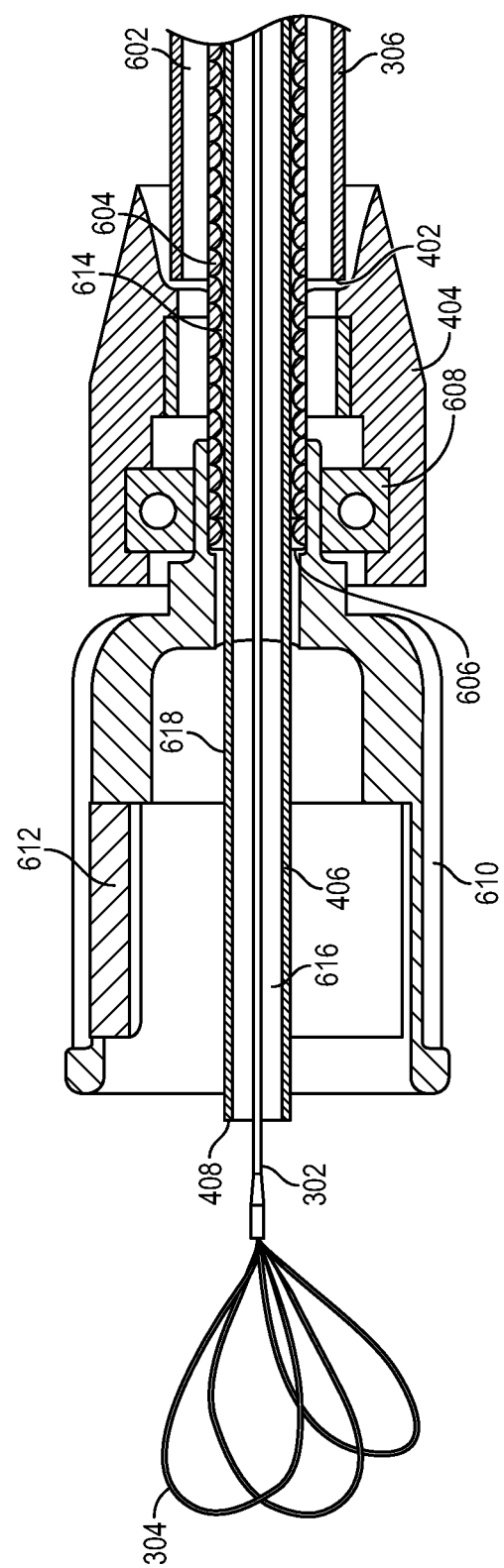
FIG. 6 is a cross-sectional view of a distal portion of a biostimulator retrieval system, in accordance with an embodiment.

Referring to FIG. 6, a cross-sectional view of a distal portion of a biostimulator retrieval system is shown in accordance with an embodiment. In cross-section, the relative radial relationship between the catheter-based system components is apparent. The outer catheter 306 has a catheter wall that surrounds an inner lumen 602. The inner lumen 602 extends distally to the distal catheter end 402, and provides a channel to receive a torque shaft 604, the cincher tube 406, and the snare 302. For example, the torque shaft 604 extends through the inner lumen 602 to a distal shaft end 606 located distal to the distal catheter end 402.

In an embodiment, the outer catheter 306 supports the docking cap 308. More particularly, the bearing housing 404 is mounted on the outer catheter 306, and contains a bearing 608 that supports the docking cap 308. The bearing 608 can be radially between the bearing housing 404 and the docking cap 308, and can hold the docking cap 308 concentrically with respect to an internal surface of the bearing housing 404. The bearing 608 allows the docking cap 308 to rotate freely relative to the bearing housing 404. The bearing 608 can be any of several types of bearings that permit radial rotation of the docking cap 308. For example, the bearing 608 can be a plain bearing, such as a bushing formed from a smooth material, e.g., polytetrafluoroethylene (PTFE). Alternatively, the bearing 608 can be a rolling-element bearing, a jewel bearing, etc. In an embodiment, the bearing 608 is a ball bearing having an inner race, an outer race, and several balls between the inner race and the outer race to allow the races to rotate freely relative to each other. The bearing 608 can be a roller bearing having several rollers. In any case, the bearing 608 can have an inner wall, e.g., an inner surface of the inner race, apposed to the docking cap 308, and an outer wall, e.g., an outer surface of the outer race, apposed to the internal surface of the bearing housing 404. Accordingly, the docking cap 308 can be rotatably coupled to the outer catheter 306 by the bearing 608.

The docking cap 308 can include a distal cup 610 portion that extends distally from the bearing housing 404. The distal cup 610 can include a docking cavity 612, which may be a generally cylindrically-shaped void within the distal cup 610. The docking cavity can be sized and configured to receive the attachment feature 220 of the biostimulator 100. Furthermore, the distal cup 610 can include a torque key feature (not shown) extending radially inward from an inner surface of the cup toward the central axis. The key feature may be located within the docking cavity to engage the attachment feature 220 and transmit torque to the biostimulator 100.

Rotational torque is transmitted from the torque shaft 604 to the key feature of the docking cap 308 through an attachment between the torque shaft 604 and the docking cap 308. More particularly, the distal shaft end 606 can be attached to the docking cap 308 within the bearing housing 404. In an embodiment, the torque shaft 604 is fixed to the docking cap 308. For example, an adhesive or thermal weld joint may be formed between an outer surface of the torque shaft 604 and an inner surface of the docking cap 308. The attachment between the torque shaft 604 and the docking cap 308 constrains rotational movement of the components relative to each other, and allows the torque shaft 604 to transmit torque directly to the docking cap 308.

The torque shaft 604 can include a shaft lumen 614 extending through the torque shaft 604 from a proximal end to the distal shaft end 606. The shaft lumen 614 can be in communication with the docking cavity of the docking cap 308 to allow other components of the biostimulator retrieval system 300 to extend distally from the handle 312 through the torque shaft 604 and the docking cap 308 to a surrounding environment distal to the docking cap 308. For example, the cincher tube 406 can extend through the shaft lumen 614 to the distal cincher end 408. The distal cincher end 408 may be maintained at a location distal to the distal shaft end 606. For example, in an undocked configuration in which the distal snare end 502 is distal to the docking cap 308, the distal cincher end 408 may also be distal to the docking cap 308. By contrast, in a docked configuration in which the distal snare end 502 is drawn into and located within the docking cavity, the distal cincher end 408 may be within the docking cavity distal to the distal shaft end 606.

The cincher tube 406 can include a tube lumen 616 extending through the cincher tube 406 from a proximal end to the distal cincher end 408. The snare 302 can extend through the tube lumen 616 to the one or more snare loops 304. The cincher tube 406 within the torque shaft 604 can surround the snare 302 within the shaft lumen 614. More particularly, the cincher tube 406 separates the snare 302 from the torque shaft 604, and thus, isolates the snare 302 from the torque shaft 604. The cincher tube 406 can separate the snare 302 and the torque shaft 604 over an entire length of the torque shaft 604. Accordingly, the snare 302 may not be in contact with the torque shaft 604, and thus, axial movement of the snare 302 within the cincher tube 406 does not cause friction or sliding contact between an inner surface of the torque shaft 604 and an outer surface of the snare 302. Rather, the cincher tube 406 has a tube wall 618 in sliding contact with the snare 302 within the shaft lumen 614.

The cincher tube 406 and the tube wall 618 is independent from and longitudinally movable relative to the torque shaft 604. Accordingly, when the snare 302 is advanced or retracted relative to the cincher tube 406, friction is between the snare 302 and the tube wall 618. Similarly, when the cincher tube 406 is advanced or retracted relative to the torque shaft 604, friction is between the cincher tube 406 and the torque shaft 604. As described below, the cincher tube 406 structure can facilitate smooth actuation and movement between the cincher tube 406, the snare 302, and the torque shaft 604. The cincher tube 406 structure can also balance the smooth actuation with pushability to allow the cincher tube 406 to press against the attachment feature 220 when the docking button is grasped and retained within the closed snare loop(s) 304.

Figure 7:
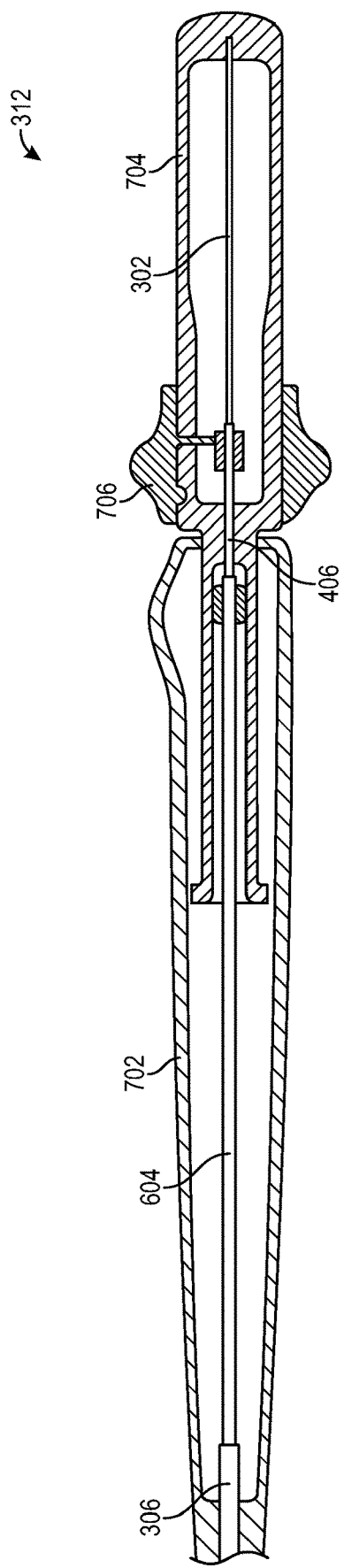
FIG. 7 is a partial cross-sectional view of a handle of a biostimulator retrieval system, in accordance with an embodiment.

Referring to FIG. 7, a partial cross-sectional view of a handle of a biostimulator retrieval system is shown in accordance with an embodiment. Axial movement between the snare 302, the cincher tube 406, the torque shaft 604, and the outer catheter 306 can be affected by the handle 312. The handle 312 includes several portions, each of which can be connected to a respective elongated member of the catheter-based system. In an embodiment, a distal handle portion 702 is coupled to the outer catheter 306. The distal handle portion 702 can remain fixed with respect to the outer catheter 306, and may be considered an axial reference point with respect to relative longitudinal position of the snare 302 or the torque shaft 604. Similarly, a proximal handle portion 704 can be coupled to the torque shaft 604, the cincher tube 406, and the snare 302. The proximal handle portion 704 can connect directly or indirectly to each of these components at locations that are proximal to the proximal end of the outer catheter 306. The proximal handle portion 704 can be coupled to the distal handle portion 702 by mechanisms that allow relative movement, e.g., axial or rotational movement, between the handle portions. The relative movement of the handle portions causes relative movement of the interconnected elongated members.

The proximal handle portion 704 may be indirectly coupled to the torque shaft 604 such that rotational movement of the proximal handle portion 704 is transmitted to the torque shaft 604, and longitudinal movement of the proximal handle portion 704 is decoupled from and not transmitted to the torque shaft 604. Accordingly, rotation, e.g., twisting, of the proximal handle portion 704 relative to the distal handle portion 702 can rotate the torque shaft 604 relative to the outer catheter 306. Such rotation can transmit torque through the torque shaft 604 to the docking cap 308 to transmit torque to the attachment feature 220 of the biostimulator 100 when unscrewing the biostimulator 100 from the target tissue.

The proximal handle portion 704 may be directly connected to the cincher tube 406 and/or the snare 302. Thus, longitudinal and rotational movement of the proximal handle portion 704 may be directly transmitted to the cincher tube 406 or the snare 302. Accordingly, longitudinal movement of the proximal handle portion 704 relative to the distal handle portion 702 can cause the distal ends of the snare 302 and the cincher tube 406 to move relative to the torque shaft 604 and the outer catheter 306. For example, the proximal handle portion 704 can be moved axially, e.g., retracted, relative to the proximal handle portion 704 to pull the distal ends of the snare 302 and the cincher tube 406 into the docking cavity from an undocked configuration to a docked configuration.

In an embodiment, the handle 312 includes a snare shroud 706 mounted on the proximal handle portion 704. The snare shroud 706 can move axially relative to the proximal handle portion 704. The snare shroud 706 can be directly connected to the cincher tube 406, and thus, movement of the snare shroud 706 can move cincher tube 406 axially relative to the snare 302. More particularly, when the snare shroud 706 is actuated, the distal cincher end 408 can be advanced toward or retracted from the distal snare end 502. This axial movement of the snare shroud 706 can cause the biostimulator retrieval system 300 to transition from the unconstrained configuration (FIG. 4) to the constrained configuration (FIG. 5) during capture of the biostimulator 100.

Figure 8:
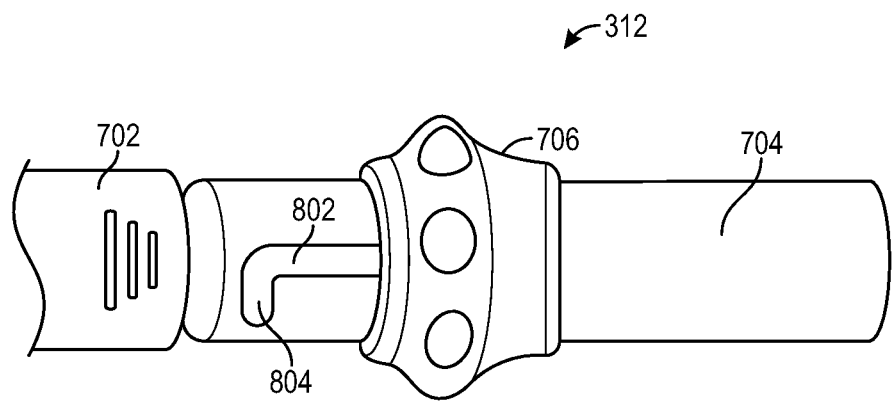
FIG. 8 is a partial side view of a handle of a biostimulator retrieval system having a snare shroud in a retracted position, in accordance with an embodiment.

Referring to FIG. 8, a partial side view of a handle of a biostimulator retrieval system having a snare shroud in a retracted position is shown in accordance with an embodiment. The biostimulator retrieval system 300 can be in the unconstrained configuration (FIG. 4) when the snare shroud 706 is at the retracted position. In the unconstrained configuration, the distal cincher end 408 may be proximally spaced relative to the snare joint 412. Retraction of the cincher tube 406 can allow the snare 302 to expand radially such that the snare loop(s) 304 open to receive the attachment feature 220 of the biostimulator 100.

Figure 9:
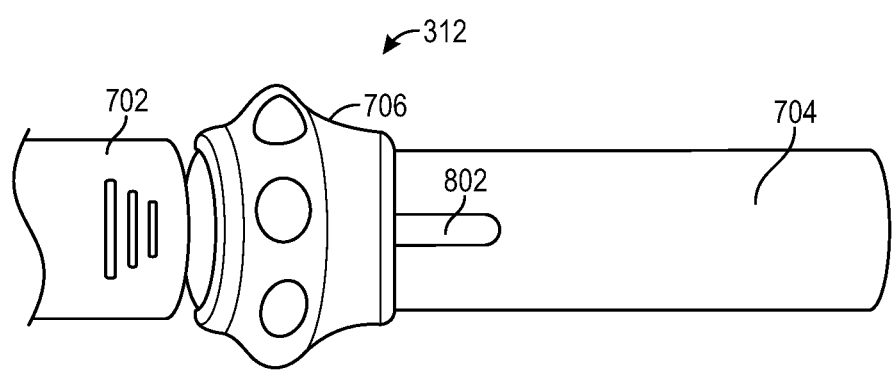
FIG. 9 is a partial side view of a handle of a biostimulator retrieval system having a snare shroud in an advanced position, in accordance with an embodiment.

Referring to FIG. 9, a partial side view of a handle of a biostimulator retrieval system having a snare shroud in an advanced position is shown in accordance with an embodiment. The snare shroud 706 can slide forward over the proximal handle portion 704 to the advanced position to transition the biostimulator retrieval system 300 from the unconstrained configuration to the constrained configuration (FIG. 5). In the constrained configuration, the distal cincher end 408 is located adjacent to the distal snare end 502. Advancement of the cincher tube 406 causes the snare 302 to collapse such that the snare loop(s) 304 close around the attachment feature 220 to capture the biostimulator 100. The travel length of the snare shroud 706 can be in a range of 15 to 25 mm, e.g., 20 mm. when the snare shroud 706 is moved all the way forward, the snare 302 is closed with the snare loop(s) 304 fully collapsed.

Referring again to FIG. 8, movement of the snare shroud 706 from the retracted position to the advanced position can be guided by a shroud slot 802 formed in the proximal handle portion 704. The shroud slot can interface with a prong (not shown) extending radially inward from the snare shroud 706. The prong can engage the slot, and thus, the prong can slide through the slot as a cam. Accordingly, rotational movement of the snare shroud 706 relative to the proximal handle portion 704 can be constrained by the prong within the shroud slot 802. The shroud slot 802 may have a primarily longitudinal segment such that the snare shroud 706 moves forward and backward in the longitudinal direction during actuation. In an embodiment, however, the shroud slot 802 can include a lock segment 804 extending in a circumferential direction around an outer surface of the proximal handle portion 704. The prong of the snare shroud 706 can be rotated from a distal end of the axial segment of the shroud slot 802 into the lock segment 804. By way of example, a lock segment 804 can extend in a counterclockwise direction from the distal end of the shroud slot 802, and thus, the snare shroud 706 can be rotated counterclockwise after being pushed forward to lock into place within the lock segment 804. Positioning the prong within the lock segment 804 acts as a lock. In the constrained configuration, a back force is applied by the attachment feature 220 captured within the snare loop(s) 304. The back force is transmitted through the cincher tube 406 to the snare shroud 706. The snare shroud 706 is therefore pushed rearward and the prong catches on the proximal face of the shroud slot 802 within the lock segment 804. The lock segment 804 catches the prong, and holds the snare shroud 706 in place, thereby keeping the snare 302 closed around the attachment feature 220.

Robust and reliable actuation of the cincher tube 406 is afforded by one or more features that provide flexibility and pushability in a component size that is compact enough to fit within the outer catheter 306 between the torque shaft 604 and the snare 302. More particularly, the cincher tube 406 can be very flexible, can move smoothly in the longitudinal direction between the snare 302 and the torque shaft 604 even when the outer catheter 306 is bent, and can have a column strength that can press forward with sufficient force to close the snare 302 around the attachment feature 220 without experiencing buckling within the tube body. Features of the cincher tube 406 that provide this balance between pushability and flexibility are described further below.

Figure 10:
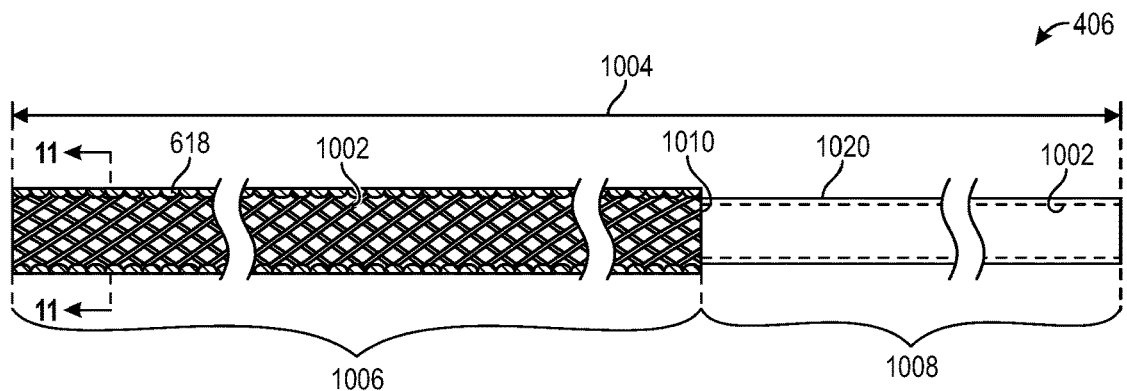
FIG. 10 is a side view of a cincher tube of a biostimulator retrieval system, in accordance with an embodiment.

Referring to FIG. 10, a side view of a cincher tube of a biostimulator retrieval system is shown in accordance with an embodiment. A structure and material of the cincher tube 406 inner and/or outer surfaces can promote smooth movement in the longitudinal direction. In an embodiment, the tube wall 618 of the cincher tube 406 has a solid inner surface 1002 over a tube length 1004 of the cincher tube 406. More particularly, an entire length of the tube length 1004 can have no interruptions, voids, breaks, gaps, slots, etc. The solid surface can be smooth, and thus, may experience low friction between the tube wall 618 and the snare 302. Similarly, the tube wall 618 of the cincher tube 406 can have a solid outer surface. As described below, the material of the outer surface may be the same as or different from the material of the inner surface 1002. In either case, the solid surface can be smooth, and thus, may experience low friction between the tube wall 618 and the torque shaft 604. The solid inner and outer surfaces of the cincher tube 406 may be contrasted with a braided structure, such as the structure of the torque shaft 604, which has an increased likelihood of abrading or catching on the snare 302 or outer catheter 306.

The cincher tube 406 can include one or more tube segments, each of which may have a single-layered or multi-layered wall. Each layer of the segments having exposed surfaces can be formed from a material that is selected to have reduced friction against one or more of the torque shaft 604 or the snare 302. By way of example, the layer(s) may be formed from polytetrafluoroethylene (PTFE), polyimide, polyether block amide (PEBA), stainless steel, or a combination thereof. The material choices allow for low friction with the snare 302, and can also contribute to pushability of the cincher tube 406 in the longitudinal direction.

An entire length of the cincher tube 406 may have a uniform structure. For example, the cincher tube 406 can have a multi-layered structure extending from a proximal end to the distal cincher end 408, which can be a length of about 50 inches. A uniform polymeric structure, however, could increase a likelihood of component shrinkage, difficulty in manufacturing the system, and a reduced closing force of the snare 302 due to pushability constraints of such a design. Accordingly, to enhance pushability of the cincher tube 406, one segment of the tube may be more stiff than another segment of the tube.

In an embodiment, the cincher tube 406 includes a distal tube portion 1006 coupled to a proximal tube portion 1008. The distal tube portion 1006 can be more flexible than the proximal tube portion 1008. The stiffer proximal tube portion 1008 allows longitudinal force to be transmitted efficiently to the distal tube portion 1006 with minimal axial compression. By contrast, the distal tube portion 1006 may experience more compressive strain than the proximal tube portion 1008, however, it may have a more flexible construction, allowing it to track through tortuous bends to the target site.

The tube portions can be connected to each other at a tube junction 1010. In an embodiment, the tube junction includes an overlap between the tubes. Alternatively, the tubes can be joined at the tube junction at their ends. Whether the tubes are joined by lap or butt joints, the components may be fixed to each other using adhesive or thermal welds. The tube joint can be proximal to the distal catheter end 402 and spaced far enough from the docking cap 308 to ensure good trackability of the system through a target anatomy. In an embodiment, the tube junction is located in a range of 10 to 20 inches, e.g., 12 inches, proximal to the distal cincher end 408. Again, such a feature may optimize the pushability and flexibility of the biostimulator retrieval system 300.

In an embodiment, the tube wall 618 in the proximal tube portion 1008 includes a metallic tube 1020. For example, the proximal tube portion 1008 can include a stainless steel hypotube having an outer diameter that forms a slip fit with an inner diameter of the distal tube portion 1006. A wall thickness of the proximal tube portion 1008 can facilitate sliding movement of the snare 302 within the proximal tube portion 1008. By way of example, the outer diameter of the proximal tube portion 1008 can be 0.043 inch, and the wall thickness can be 0.005 inch.

Figure 11:
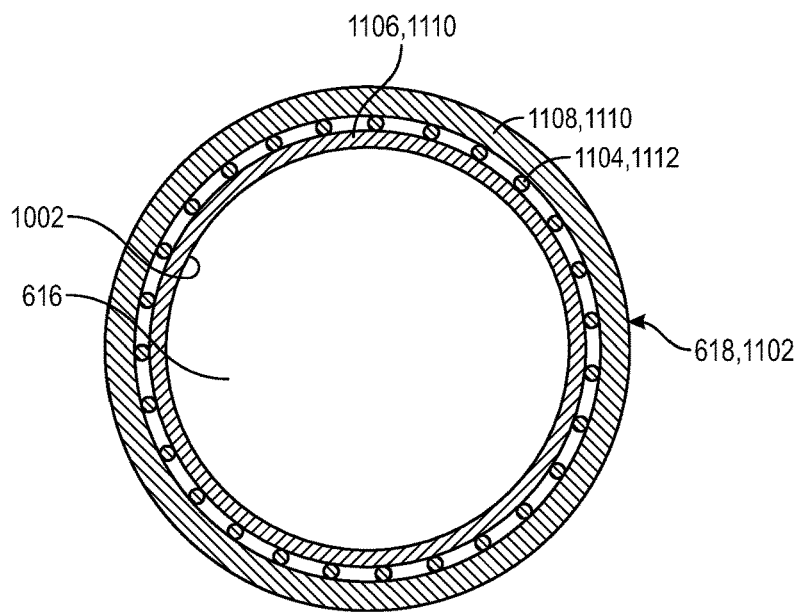
FIG. 11 is a cross-sectional view, taken about line A-A of FIG. 10, of a cincher tube of a biostimulator retrieval system, in accordance with an embodiment.

Referring to FIG. 11, a cross-sectional view, taken about line A-A of FIG. 10, of a cincher tube of a biostimulator retrieval system is shown in accordance with an embodiment. In an embodiment, the tube wall 618 in the distal tube portion 1006 has several tubular layers 1102. For example, the tubular layers 1102 can include a support layer 1104 and one or more of an inner layer 1106 or an outer layer 1108. The layers of the distal tube portion 1006 can impart respective structural characteristics to the cincher tube 406. For example, the inner layer 1106 material and/or outer layer 1108 material may be polymer layers 1110 that provide flexibility and low friction against external surfaces. By contrast, the support layer 1104 can include a supportive structure, such as a tubular braid 1112, that enhances pushability of the cincher tube 406. The one or more polymer layers 1110 on the support layer 1104 may be solid layers having the solid inner or outer surface characteristics described above. In an embodiment, the polymer layers 1110 completely isolate the support layer 1104 from the surrounding environment. By way of example, the tubular braid 1112 can be sandwiched (as shown), embedded, or encapsulated by the one or more polymer layers 1110. The encapsulated tubular braid 1112 (or other support layer structure) may not be exposed anywhere along the tube length 1004 of the cincher tube 406, nor at the end of the cincher tube 406. Encapsulation of the support layer 1104 can be achieved in a coextrusion process, for example.

It is contemplated that, just as the tube segments may have differing flexibilities, each of the polymer layers 1110 may also have respective flexibilities that differ from one another. In an embodiment, the polymer layers 1110 include the outer layer 1108 and the inner layer 1106, and the outer layer 1108 may be more flexible than the inner layer 1106. For example, the inner layer 1106 may be formed from a composite material of PTFE and polyimide, and the outer layer 1108 may be formed from polyimide or PEBA (e.g., 55D, 63D, or 72D PEBA). In any case, the inner layer material can be less flexible than the outer layer 1108 material.

In an embodiment, the inner layer 1106 has a more lubricious material than the outer layer 1108. For example, the inner layer 1106 may be formed from a composite material of PTFE and polyimide, and the outer layer 1108 may be formed from polyimide or PEBA (e.g., 55D, 63D, or 72D PEBA). In any case, the outer layer 1108 material can be less lubricious than the inner layer material.

It is contemplated that in some embodiments the cincher tube 406 may have only one of the inner layer 1106 or the outer layer 1108. For example, the cincher tube 406 may have an inner layer 1106 constructed from a composite of PTFE and polyamide on an inner side of the support layer 1104, and may have no outer layer 1108. Similarly, the distal tube portion 1006 may have a single-layered wall formed entirely from a composite of PTFE and polyamide, or from PEBA, e.g., 72D PEBA. In an embodiment, the cincher tube 406 may have an outer layer 1108 constructed from polyethylene terephthalate (PET) on an outer side of the support layer 1104, and may have no inner layer 1106. Other structures that balance pushability and flexibility may be contemplated by one skilled in the art.

Figure 12:
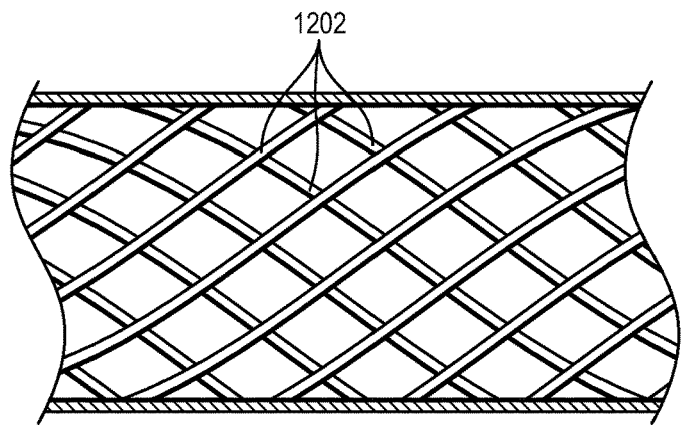
FIG. 12 is a side view of a support layer of a cincher tube of a biostimulator retrieval system, in accordance with an embodiment.

Referring to FIG. 12, a side view of a support layer of a cincher tube of a biostimulator retrieval system is shown in accordance with an embodiment. The support layer 1104, which is between the outer layer 1108 and the inner layer 1106, can include a metallic strand 1202. For example, the metallic strand 1202 can be in a coil extending over the tube length 1004. The coil can be formed from a 304V stainless steel strand, by way of example. In an embodiment, the coil is a closed pitch coil. Optionally, the cincher tube 406 is constructed entirely from the support layer 1104 and has no polymer layers 1110. More particularly, one or both of the proximal and distal cincher tube segments can have one or more layers of metallic coils or braids that are not covered by a polymer jacket.

In an embodiment, the support layer 1104 includes the tubular braid 1112 having the metallic strand 1202 as one of several metallic strands 1202 interlaced in a braid structure. The tubular braid 1112 can have a per inch cross (PIC) count that imparts adequate column strength and pushability to the cincher tube 406. By way of example, the braid can have a PIC count between 50 to 150 PIC, e.g., 70, 90, or 120 PIC.

The cincher tube 406 may have a cross-sectional profile that facilitates smooth advancement and retraction through the torque shaft 604. More particularly, the tube wall 618 may have a dimension that is minimized to achieve clearance between the tube surfaces and both the snare 302 and the torque shaft 604. To reduce the wall profile without sacrificing pushability, the metallic strand(s) of the support layer 1104 may have a cross-sectional area that is noncircular. For example, the metallic strand 1202 can have a rectangular or an elliptical cross-sectional profile. Such a flat strand includes a thickness in a radial direction that is less than a width of the strand in a circumferential direction. The flattened profile can achieve adequate longitudinal and circumferential stiffness of the strand while reducing the profile of the strand in the radial direction as compared to a round strand profile. Thus, the flat wire structure contributes to the cincher tube 406 that can fit within the tight space constraints while maintaining pushability.

Figure 13:
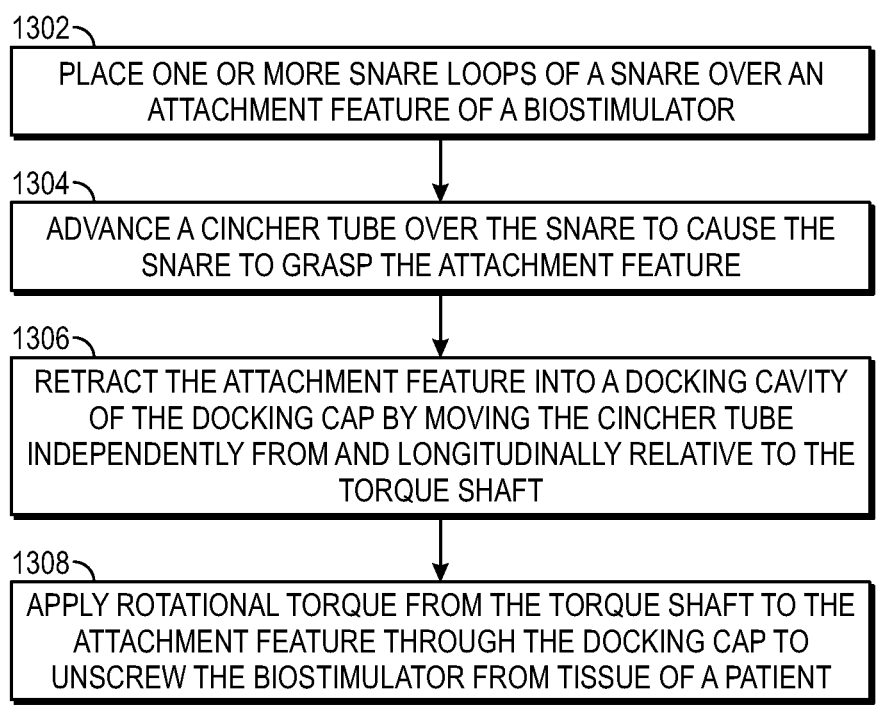
FIG. 13 is a flowchart of a method of capturing and unscrewing a biostimulator from tissue of a patient using a biostimulator retrieval system, in accordance with an embodiment.

Referring to FIG. 13, a flowchart of a method of capturing and unscrewing a biostimulator from tissue of a patient using a biostimulator retrieval system is shown in accordance with an embodiment. The biostimulator retrieval system 300 can have the structure described above, and thus, the flowchart is illustrative of the method that can be achieved using the prescribed structure. For example, the cincher tube 406 can be moved independently from and longitudinally relative to the torque shaft 604 that applies torque to the docking cap 308.

The biostimulator retrieval system 300 can be tracked through a vasculature of the patient until the distal end of the system is located near the biostimulator 100, which was previously implanted into the target tissue of the patient. At operation 1302, one or more of the snare loops 304 are placed over the attachment feature 220 of the biostimulator 100. The snare loop(s) 304 can be in an expanded state, e.g., when the system is in the unconstrained configuration, as shown in FIG. 4.

At operation 1304, the cincher tube 406 is advanced over the snare 302 to cause the snare 302 to grasp the attachment feature 220. Advancement of the cincher tube 406 can be affected by a forward movement of the snare shroud 706 over the proximal handle portion 704. As the cincher tube 406 advances over the snare 302, it is moved to the constrained configuration shown in FIG. 5. As described above, the snare 302 is separated from the torque shaft 604 by the cincher tube 406, and the torque shaft 604 is attached to the docking cap 308. Accordingly, the snare 302 transitions from the unconstrained configuration to the constrained configuration while the torque shaft 604 remains attached to the docking cap 308.

At operation 1306, the attachment feature 220, which is captured within the closed snare 302, is retracted into the docking cavity of the docking cap 308. Retraction of the attachment feature 220 can be affected by moving the cincher tube 406 independently from and longitudinally relative to the torque shaft 604 that remains attached to the docking cap 308. The retraction may be caused by a proximal movement of the proximal handle portion 704 relative to the distal handle portion 702. When the attachment feature 220 is docked within the docking cavity, the torque key of the docking cap 308 can engage the attachment feature 220.

At operation 1308, rotational torque is applied from the torque shaft 604 to the attachment feature 220 through the docking cap 308. The torque shaft 604 can be rotated via rotation of the proximal handle portion 704 relative to the distal handle portion 702. More particularly, relative motion between the handle portions results in relative motion between the outer catheter 306 and the torque shaft 604, which results in relative rotation between the docking cap 308 and the outer catheter 306. By way of example, the relative rotation may be in a counterclockwise direction such that the anchor of the biostimulator 100 is unscrewed from the tissue of the patient. After unscrewing the biostimulator 100 from the target tissue, the biostimulator retrieval system 300 can be removed from the patient to retrieve the biostimulator 100.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:
1. A biostimulator retrieval system, comprising:
an outer catheter having an inner lumen;
a bearing housing mounted on the outer catheter, wherein the bearing housing contains a bearing;
a docking cap rotatably coupled to the outer catheter by the bearing, wherein the docking cap has a docking cavity to receive an attachment feature of a biostimulator;
a torque shaft extending through the inner lumen, wherein the torque shaft is attached to the docking cap within the bearing housing proximal to the docking cavity, and wherein the torque shaft has a shaft lumen in communication with the docking cavity;
a cincher tube extending through the shaft lumen and having a tube lumen;
a snare including one or more snare loops, wherein the snare extends through the tube lumen and is separated from the torque shaft by the cincher tube; and
a handle including
a distal handle portion coupled to the outer catheter,
a proximal handle portion slidably mounted on the distal handle portion and indirectly coupled to the torque shaft such that rotational movement of the proximal handle portion relative to the entire distal handle portion is transmitted to the torque shaft and longitudinal movement of the proximal handle portion relative to the distal handle portion is not transmitted to the torque shaft.

2. The biostimulator retrieval system of claim 1, wherein the torque shaft is fixed to the docking cap.

3. The biostimulator retrieval system of claim 1, wherein the cincher tube has a tube wall in sliding contact with the snare within the shaft lumen.

4. The biostimulator retrieval system of claim 3, wherein the tube wall has a solid inner surface over a tube length of the cincher tube.

5. The biostimulator retrieval system of claim 4, wherein the cincher tube includes a distal tube portion coupled to a proximal tube portion, and wherein the distal tube portion is more flexible than the proximal tube portion.

6. The biostimulator retrieval system of claim 5, wherein the tube wall in the distal tube portion has a plurality of tubular layers, and wherein the tube wall in the proximal tube portion includes a metallic tube.

7. The biostimulator retrieval system of claim 6, wherein the plurality of tubular layers include a support layer having a metallic strand, and one or more polymer layers on the support layer, and wherein the one or more polymer layers are solid layers.

8. The biostimulator retrieval system of claim 7, wherein a cross-sectional area of the metallic strand is non-circular.

9. The biostimulator retrieval system of claim 7, wherein the support layer includes a tubular braid having the metallic strand, and wherein the tubular braid is encapsulated by the one or more polymer layers.

10. The biostimulator retrieval system of claim 9, wherein the one or more polymer layers include an outer layer and an inner layer, wherein the support layer is between the outer layer and the inner layer, and wherein the outer layer is more flexible than the inner layer.

11. The biostimulator retrieval system of claim 1, wherein the snare is directly coupled to the proximal handle portion, and wherein the handle includes
 a snare shroud coupled to the cincher tube, wherein the snare shroud is slidably mounted on the proximal handle portion such that the cincher tube is longitudinally moveable relative to the snare.

12. A biostimulator retrieval system, comprising:
 a docking cap having a docking cavity to receive an attachment feature of a biostimulator;
 a torque shaft having a distal shaft end fixed to the docking cap, wherein the torque shaft has a shaft lumen in communication with the docking cavity;
 a snare including one or more snare loops, wherein the snare extends through the shaft lumen and the docking cavity;
 a cincher tube surrounding the snare within the shaft lumen, wherein the cincher tube is independent from and longitudinally moveable relative to the torque shaft, and wherein the cincher tube has a distal cincher end distal to the distal shaft end when the attachment feature is received within the docking cavity; and
 a handle including a proximal handle portion coupled to the torque shaft and a snare shroud mounted on the proximal handle portion, wherein the handle includes a lock slot segment in an outer surface of the proximal handle portion, and wherein the lock slot segment receives a portion of the snare shroud such that rotation of the snare shroud relative to the proximal handle portion within the lock slot segment locks the snare relative to the cincher tube.

13. The biostimulator retrieval system of claim 12, wherein the cincher tube has a tube wall in sliding contact with the snare within the shaft lumen.

14. The biostimulator retrieval system of claim 13, wherein the tube wall has a solid inner surface.

15. The biostimulator retrieval system of claim 14, wherein the cincher tube includes a distal tube portion coupled to a proximal tube portion, wherein the tube wall in the distal tube portion is more flexible than the tube wall in the proximal tube portion, wherein the tube wall in the distal tube portion has a plurality of tubular layers, and wherein the tube wall in the proximal tube portion includes a metallic tube.

16. The biostimulator retrieval system of claim 15, wherein the plurality of tubular layers include a support layer having a metallic strand, and one or more polymer layers on the support layer, and wherein the one or more polymer layers are solid layers.

17. The biostimulator retrieval system of claim 16, wherein a cross-sectional area of the metallic strand is non-circular.

18. The biostimulator retrieval system of claim 16, wherein the support layer includes a tubular braid having the metallic strand, and wherein the tubular braid is encapsulated by the one or more polymer layers.

19. The biostimulator retrieval system of claim 18, wherein the one or more polymer layers include an outer layer and an inner layer, wherein the support layer is between the outer layer and the inner layer, and wherein the outer layer is more flexible than the inner layer.

* * * * *